(12) United States Patent
Shin

(10) Patent No.: US 12,324,746 B2
(45) Date of Patent: Jun. 10, 2025

(54) IMPLANT, SYSTEM INCLUDING IMPLANT, AND METHOD OF USING SYSTEM

(71) Applicant: GS Solutions, Inc., Mission Viejo, CA (US)

(72) Inventor: Hanjin Shin, Mission Viejo, CA (US)

(73) Assignee: GS Solutions, Inc., Santa Ana, CA (US)

( * ) Notice: Subject to any disclaimer, the term of this patent is extended or adjusted under 35 U.S.C. 154(b) by 801 days.

(21) Appl. No.: 17/589,602

(22) Filed: Jan. 31, 2022

(65) Prior Publication Data

US 2023/0157838 A1 May 25, 2023

Related U.S. Application Data

(60) Provisional application No. 63/144,082, filed on Feb. 1, 2021.

(51) Int. Cl.
*A61F 2/44* (2006.01)
*A61F 2/00* (2006.01)
*A61F 2/46* (2006.01)
*A61F 2/30* (2006.01)

(52) U.S. Cl.
CPC .......... *A61F 2/4455* (2013.01); *A61F 2/0095* (2013.01); *A61F 2/4611* (2013.01); *A61F 2002/30324* (2013.01); *A61F 2002/30406* (2013.01); *A61F 2002/30477* (2013.01); *A61F 2002/30495* (2013.01); *A61F 2002/4615* (2013.01); *A61F 2002/4627* (2013.01)

(58) Field of Classification Search
CPC ...... A61F 2/442; A61F 2/4425; A61F 2/4611; A61F 2/0095; A61F 2002/30324; A61F 2002/30495; A61F 2002/4615; A61F 2002/4627
USPC ........................................... 623/17.11–17.16
See application file for complete search history.

(56) References Cited

U.S. PATENT DOCUMENTS

| | | | | |
|---|---|---|---|---|
| 11,534,307 | B2 * | 12/2022 | Struck | A61F 2/4611 |
| 2009/0105830 | A1 * | 4/2009 | Jones | A61B 17/8042 |
| | | | | 606/301 |
| 2012/0136392 | A1 * | 5/2012 | Keegan | A61B 17/808 |
| | | | | 606/279 |

OTHER PUBLICATIONS

Nexxt Matrixx Stand Alone Cervical, TL System, Surgical Technique Guide; 71-042, Rev. B; accessed Nov. 11, 2021; pp. 1-21; www.nexxtspine.com; Nexxt Spine, LLC, Noblesville, IN.
Zavation Z-Link Cervical, Surgical Technique for Zavation Z-Link Cervical; ST-008 Rev 0; accessed Nov. 11, 2021; pp. 1-13; Zavation LLC, Flowood, MS.

* cited by examiner

*Primary Examiner* — Eduardo C Robert
*Assistant Examiner* — Christina Negrellirodriguez

(57) ABSTRACT

An implant includes a plate having a plurality of fastener holes, the plurality of fastener holes being configured to receive a plurality of fasteners, respectively; a spacer coupled to the plate and configured to be inserted into a treatment region; and a fastener lock movably coupled to the plate and configured to lock the plurality of fasteners.

18 Claims, 10 Drawing Sheets

IMPLANT, SYSTEM INCLUDING IMPLANT, AND METHOD OF USING SYSTEM

CROSS-REFERENCE TO RELATED APPLICATION

The present disclosure claims priority to U.S. provisional Application No. 63/144,082 filed on Feb. 1, 2021, which is incorporated by reference herein for all purposes.

BACKGROUND

The present disclosure relates to an implant for treating spinal disorders, a system including the implant, and a method of using the system during surgery.

An implant may be used to fuse a pair of adjacent vertebrae in a cervical spine. An inserting device may be used to place the implant in a treatment region (e.g., a gap between the adjacent vertebrae). When the inserting device is coupled to the implant, for example, by gripping both sides of the implant, the treatment region may not be sufficiently visible to a surgeon during surgery. After placing the implant in the gap between the vertebrae and inserting screws through the implant to fix it to the vertebrae, the surgeon may place a screw lock for keeping the inserted screws in place over the fixed implant to combine the screw lock with the implant.

SUMMARY

Embodiments of the present disclosure relates to an implant and a system thereof.

In an embodiment, an implant includes a plate having a plurality of fastener holes, the plurality of fastener holes being configured to receive a plurality of fasteners, respectively; a spacer coupled to the plate and configured to be inserted into a treatment region; and a fastener lock movably coupled to the plate and configured to lock the plurality of fasteners. The fastener lock may include a ring portion rotatably coupled to a hole of the plate disposed substantially at the central location of the plate.

In an embodiment, a system includes an implant; and an inserter configured to be removably coupled to the implant and insert the implant into a treatment region. The implant includes a plate having a plurality of fastener holes, the plurality of fastener holes being configured to receive a plurality of fasteners, respectively; a spacer coupled to the plate; and a fastener lock movably coupled to the plate and configured to lock the plurality of fasteners. The fastener lock may include a ring portion rotatably coupled to a hole of the plate disposed substantially at the central location of the plate.

In an embodiment, a method includes coupling an inserter to a plate of an implant by rotating the inserter; inserting the implant into a treatment region; fastening the implant using a plurality of fasteners; and securing the plurality of fasteners with a fastener lock of the implant by rotating the inserter.

DESCRIPTION

Figure 1A:
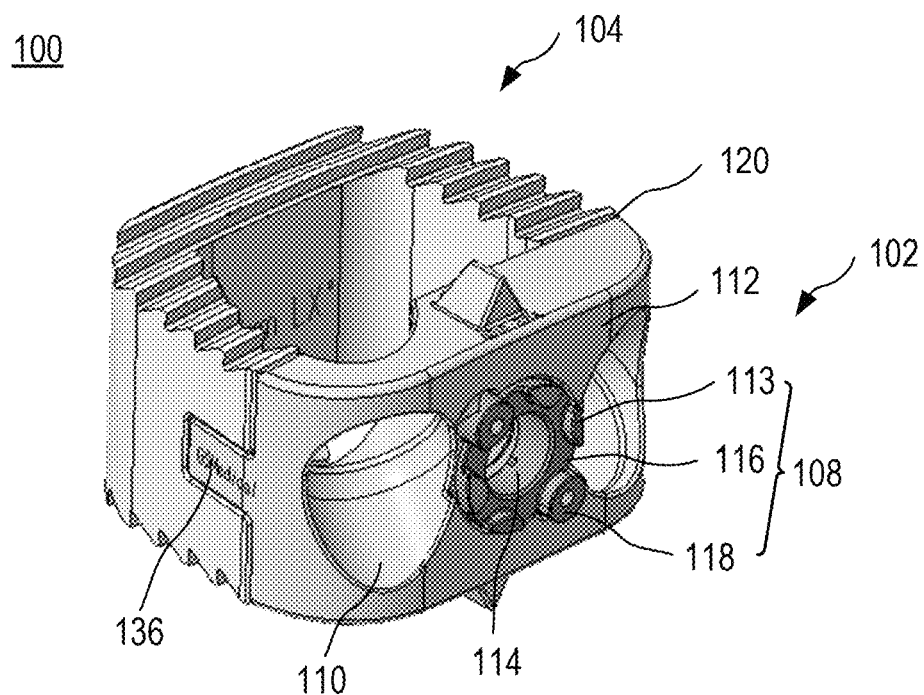
FIGS. 1A, 1B, and 1C illustrate a perspective view, a top view, and an exploded view of an implant, respectively, according to an embodiment of the present disclosure.

In the following description, certain illustrative embodiments have been illustrated and described. As those skilled in the art would realize, these embodiments may be modified in various different ways without departing from the scope of the present disclosure. Accordingly, the drawings and description are to be regarded as illustrative in nature and not restrictive. Like reference numerals designate like elements in the specification.

FIG. 1A illustrates a perspective view of an implant (e.g., a cervical spine implant) 100 according to an embodiment of the present disclosure. The implant 100 may be inserted in a gap of a patient's spine and can occupy the gap. For example, the implant 100 may occupy a gap between adjacent cervical vertebrae with a spacer and be anchored to each vertebra with fasteners (e.g., screws). The implant 100 may have a plate 102, a spacer 104, and a fastener lock (e.g., a screw lock) 108.

The plate 102 may have at least two fastener holes (e.g., screw holes) 110. The screw holes 110 may be angled such that each of the screw holes 110 directs a corresponding screw (not shown) into a vertebra in a specific direction. In the embodiment shown in FIG. 1A with two screw holes 110, one of two screws may be screwed into an upper vertebra and the other of the screws may be screwed into a lower vertebra. The screws may be inserted into the screw holes 110 from a first end (e.g., a proximal end) 112 of the plate 102. The spacer 104 may be attached to a second end (e.g., a distal end) 120 of the plate 102.

The plate 102 may further have a hole 114. In an embodiment, the hole 114 may be threaded. The hole 114 may engage with an inserter (e.g., an inserter 800 shown in FIG. 8) that is used to insert the implant 100 between the vertebrae. In an embodiment, the hole 114 is disposed at the center or substantially at the central location of the plate 102. Such an inserter may engage with the hole 114 that is disposed substantially at the central location of the plate 102 and has a relatively small size, thereby increasing visibility of a treatment region (e.g., the gap between the vertebrae) during surgery compared to when a conventional inserter grips both sides of a conventional implant to insert the conventional implant during surgery. For illustrative convenience, the hole 114 may be referred to as a "central hole."

The screw lock 108 may be movably coupled to the plate 102 such that the screw lock 108 may be disposed over the central hole 114 at the proximal end 112 of the plate 102. The screw lock 108 may be movably coupled to the plate 102 in advance to form an integrated unit together, thereby obviating the need to combine a separate screw lock with the plate 102 during surgery.

In an embodiment, the screw lock 108 may have a ring portion 116 and a plurality of flaps 118. The ring portion 116 may be rotatably coupled to the central hole 114, and may have a plurality of protrusions 113.

The flaps 118 may extend from the ring portion 116 in a given direction (e.g., a radial direction). The flaps 118 may be positioned over the screws by rotating the ring portion 116 using the inserter. For example, when the inserter is used to rotate the ring portion 116 in a given rotational direction (e.g., a counter clockwise direction), a portion of each of the flaps 118 may be positioned over each of the screws 106, thereby substantially prevent the screws from coming out in a proximal direction.

In an embodiment, the number of the flaps 118 may correspond to that of the screw holes 110 and be spaced apart from each other at regular intervals. For example, in the embodiment of FIG. 1A, the number (e.g., two) of the flaps 118 may correspond to that of the screw holes 110, respectively, and the flaps 118 may be disposed opposite to each other with respect to a center of the ring portion 116. In an embodiment, the flaps 118 and the protrusions 113 may be arranged to define a plurality of recesses that match an engaged portion (e.g., a second hollow end 820 in FIG. 8B) of the inserter to facilitate rotation of the ring portion 116 by the inserter. For example, in the embodiment of FIG. 1A, two flaps 118 and four protrusions 113 may be disposed along a circumference of the ring portion 116 at regular intervals.

Figure 1B:
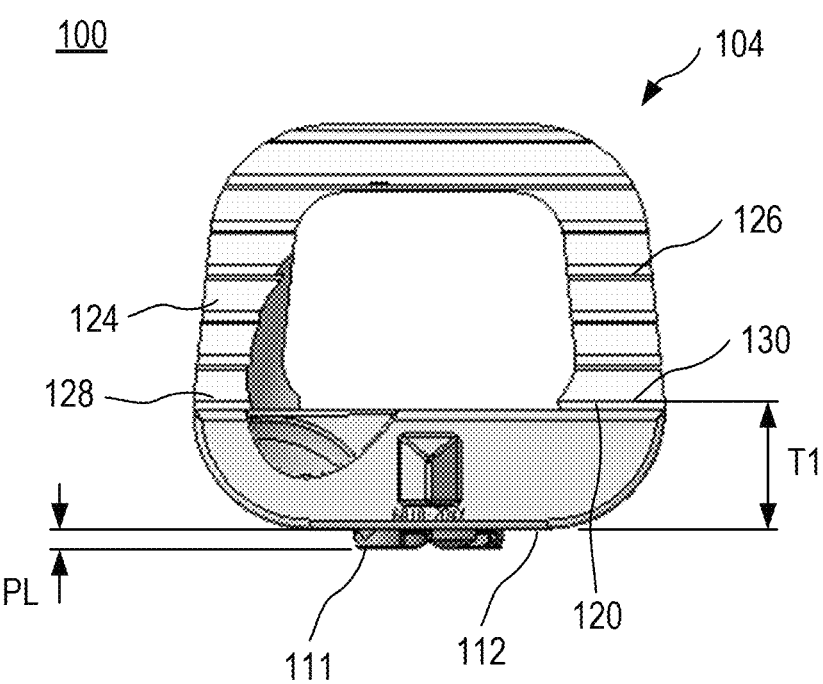

FIG. 1B illustrates a top view of the implant 100 according to an embodiment of the present disclosure. The plate 102 may have a relatively small thickness T1 between the distal end 120 and the proximal end 112. For example, when the hole 114 of the plate 102 has a substantially cylindrical shape, the thickness T1 of the plate may be defined in an axial direction of the hole 114 of the plate 102. The screw lock 108 may also have a relatively small thickness between a distal end (not shown) and a proximal end 111, a portion including the distal end of the screw lock 108 being inserted into an opening of the plate 102. For example, when the ring portion 116 of the screw lock 108 has a substantially annular cylindrical shape, the thickness of the screw lock 108 may be defined in an axial direction of the ring portion 116. In an embodiment, a ratio of the thickness of the screw lock 108 over the thickness T1 of the plate 102 may be between 0.15 to 0.35. When the ratio is greater than 0.35, the implant 101 including the plate 102 and the screw lock 108 may not have a sufficiently small thickness to be properly installed into the treatment region. In contrast, when the ratio is smaller than 0.15, the flaps 118 may not have structural properties (e.g., e.g., bending modulus to resist a bending moment resulting from a screw loosened in the proximal direction) sufficient to properly keep the screw in place. In an embodiment, the screw lock 108 may have the thickness sufficient to make a proximal end 111 of the screw lock 108 protrude from the proximal end 112 of the plate 102 by a given length (e.g., less than 1 mm) PL In the embodiment of FIG. 1B, the spacer 104 may be U-shaped. The spacer 104 may include a first leg 124 having a first end 128 and a second leg 126 having a second end 130. The spacer 104 may be coupled to the plate 102. For example, the first end 128 and the second end 130 of the spacer 104 may directly contact the distal end 120 of the plate 102. Although the U-shaped spacer 104 is shown in FIG. 1B, embodiments of the present disclosure are not limited thereto, and the spacer 194 may have various shapes according to embodiments.

Figure 1C:
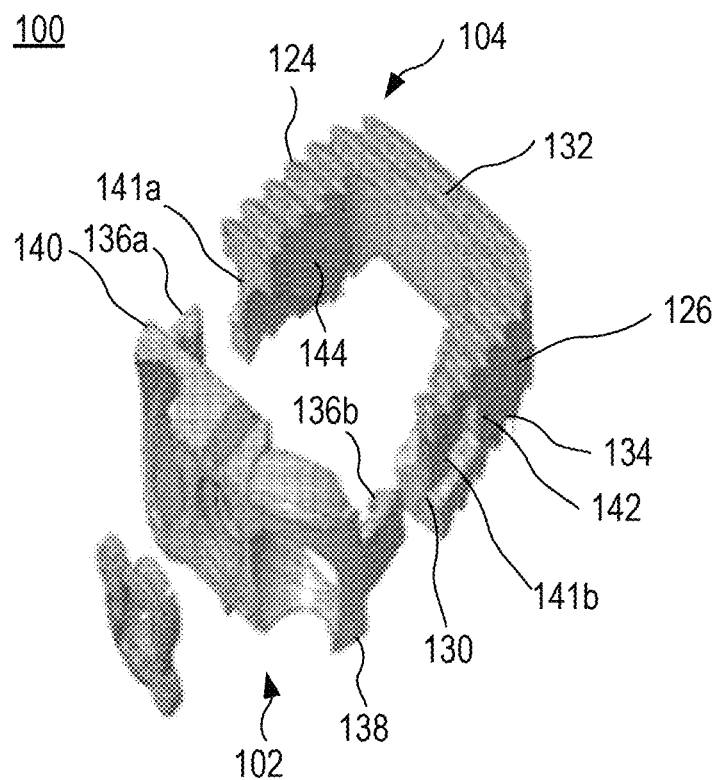

FIG. 1C illustrates an exploded view of the implant 100 according to an embodiment of the present disclosure. The spacer 104 may have an upper surface 132 and a lower surface 134. The upper surface 132 and the lower surface 134 may directly contact an upper vertebra and a lower vertebra, respectively, once the implant 100 is implanted. The upper surface 132 and the lower surface 134 may be rough. For example, the upper surface 132 and the lower surface 134 may be jagged, serrated, or knurled, thereby substantially preventing slippage of the spacer 104 between the vertebrae with sufficient friction. For example, the spacer 104 may include polyetheretherketone (PEEK), hydroxyapatite (HA)-PEEK, titanium (Ti), or the like. The plate 102 may have a pair of first coupling parts (e.g., male fastener parts) 136a and 136b respectively extending from a first end 138 and a second end 140 of the plate 102 in a distal direction. Each of the male fastener parts 136 may be a clip, a hook, a pin, or the like. The first and second legs 124 and 126 of the spacer 104 may have a pair of second coupling parts (e.g., female fastener parts) 141a and 141b to be removably coupled to the pair of first coupling parts 136a and 136b. The female fastener parts 141a and 141b may be shaped and sized to receive the male fastener parts 136a and 136b, respectively. Although the female fastener parts 141a and 141b may be on an exterior 142 of the spacer 104 as shown in FIG. 1C, embodiments of the present disclosure are not limited thereto. For example, the female fastener parts 141a and 141b may be on an interior 144 of the spacer 104. Although the plate 102 has the male fastener parts 136a and 136b and the spacer 104 has the female fastener parts 141a and 141b, as shown in the embodiment of FIG. 1C, embodiments of the present disclosure are not limited thereto. In other embodiments, the spacer 104 may have the male fastener parts and the plate 102 may have the female fastener parts.

Figure 2:
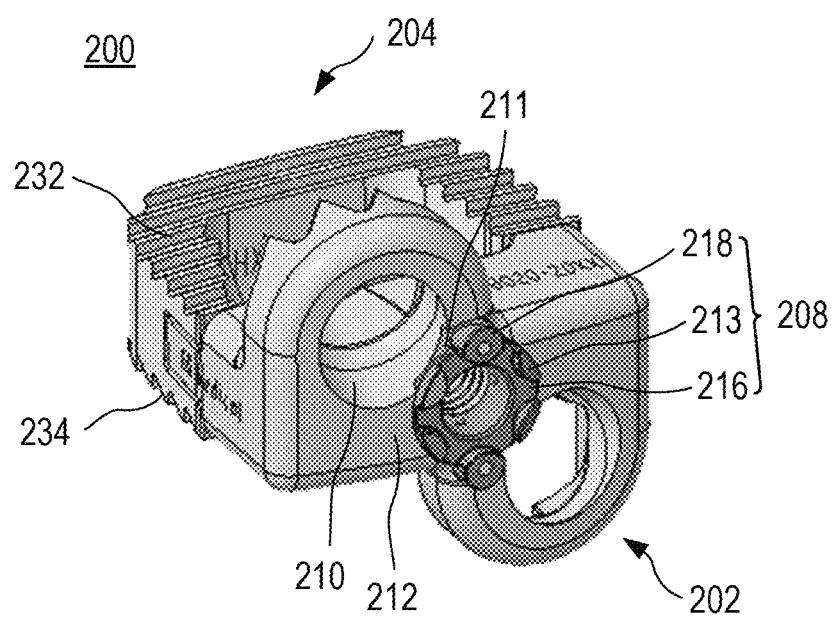
FIG. 2 illustrates a perspective view of an implant according to an embodiment of the present disclosure.

FIG. 2 illustrates a perspective view of an implant 200 according to an embodiment of the present disclosure. The implant 200 may have substantially the same features as those of the implant 100 of FIGS. 1A-1C, except that the implant 200 has a plate 202 different from the plate 102 of the implant 100 shown in FIGS. 1A-1C. Specifically, the implant 200 in FIG. 2 may have the plate 202 having two offset screw holes 210. The screw holes 210 may be disposed symmetrically with respect to a center of the plate 202. For example, the screw holes 210 may located in diagonally opposite corners of the plate 402, respectively. The screw holes 210 may be positioned with respect to the vertebrae such that a single screw (not shown) is screwed into each vertebra. For example, the screw holes 210 may direct a pair of screws may be screwed into an adjacent pair of vertebrae, respectively.

The plate 202 may have one or more recesses 211 on its proximal end 212 to allow each flap 218 of the screw lock 208 to rotate through a corresponding one of the recesses 211. The recesses 211 may be contiguous to the screw holes 210, respectively, to allow the flaps 218 to be positioned over respective screws (not shown) when the screw lock 208 rotates in a given rotational direction (e.g., a counter clockwise direction), thereby locking the screws in place.

Figure 3:
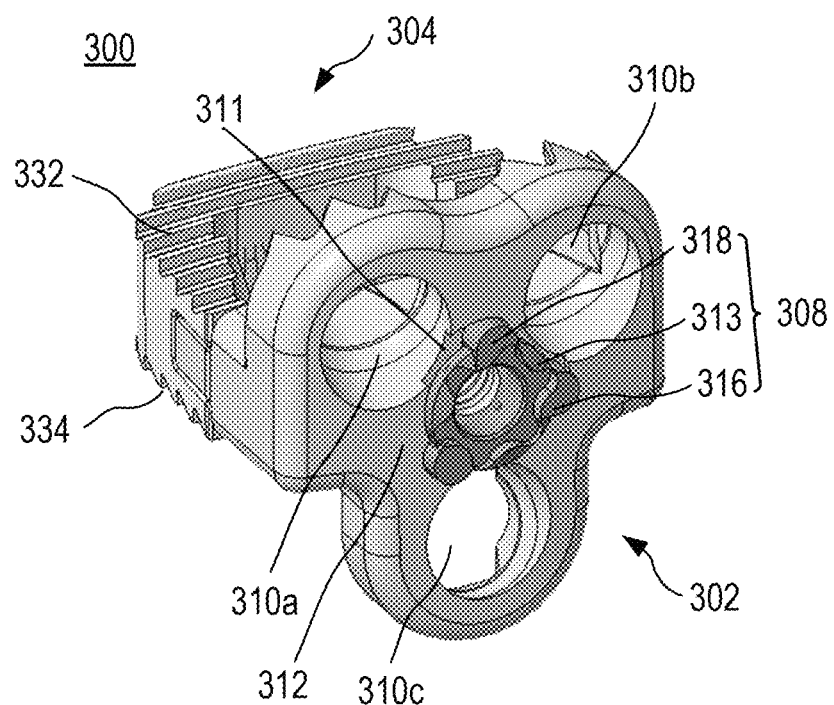
FIG. 3 illustrates a perspective view of an implant according to an embodiment of the present disclosure.

FIG. 3 illustrates a perspective view of an implant 300 according to an embodiment of the present disclosure. The implant 300 may have substantially the same features as those of the implant 100 of FIGS. 1A-1C, except that the implant 300 has a plate 302 different from the plate 102 of the implant 100 shown in FIGS. 1A-1C. Specifically, the implant 300 in FIG. 3 may have the plate 302 having three screw holes 310a to 310c. The screw holes 310a to 310c may be arranged such that first and second screw holes 310a and 310b are located in adjacent corners of the plate 302 and a third screw hole 310c is located centrally and opposite from the first and second screw holes 310a and 310b. The first and second screw holes 310a and 310b may direct two screws (not shown) into a first vertebra (e.g., an upper vertebra), and the third screw hole 310c may direct a screw (not shown) into a second vertebra (e.g., a lower vertebra) that is adjacent to the first vertebra.

The plate 302 may have one or more recesses 311 on its proximal end 312 to allow each flap 318 of the screw lock 308 to rotate through a corresponding one of the recesses 311. The recesses 311 may be contiguous to the screw holes 310a to 310c, respectively, to allow the flaps 318 to be positioned over respective screws (not shown) when the screw lock 308 rotates in a given rotational direction (e.g., a counter clockwise direction), thereby locking the screws in place. In the embodiment shown in FIG. 3, the number of the flaps 318 may be three to correspond to that of the screw holes 310a to 310c, and each of three protrusions 313 is disposed between a corresponding pair of adjacent flaps 318.

Figure 4:
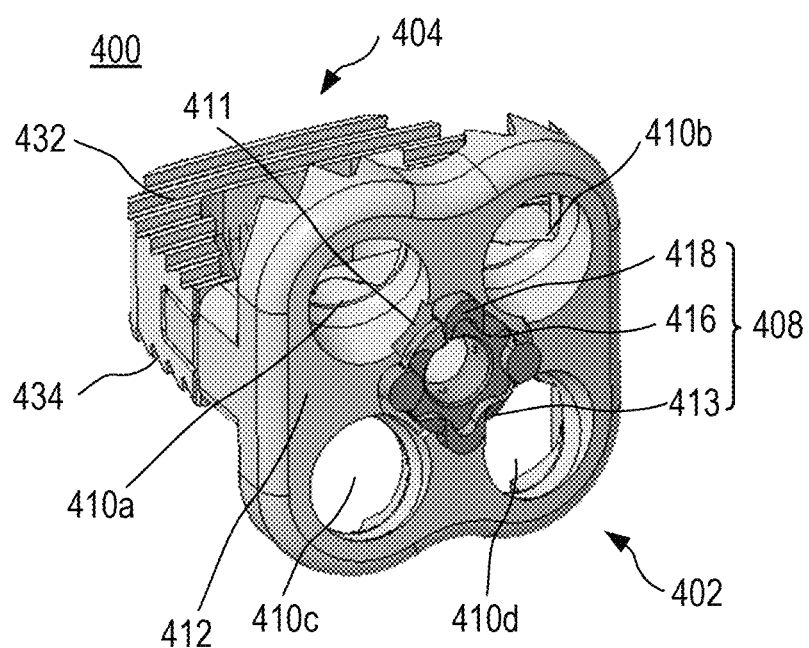
FIG. 4 illustrates a perspective view of an implant according to an embodiment of the present disclosure.

FIG. 4 illustrates a perspective view of an implant 400 according to an embodiment of the present disclosure. The implant 400 may have substantially the same features as those of the implant 100 of FIGS. 1A-1C, except that the implant 400 has a plate 402 different from the plate 102 shown in FIGS. 1A-1C. Specifically, the implant 400 in FIG. 4 may have the plate 402 having first to fourth screw holes 410a to 410d. Each of the screw holes 410a to 410d may be located at a corresponding one of the four corners of the plate 402. The screw holes 410a to 410d may be aligned with the vertebrae such that two screws (not shown) are screwed into each vertebra. For example, the first and second screw holes 410a and 410b may direct two screws (not shown) into a first vertebra (e.g., an upper vertebra), and the third and fourth screw holes 410c and 410d may direct the remaining two screws (not shown) into a second vertebra (e.g., a lower vertebra) that is adjacent to the first vertebra. The screw holes 410a to 410d may be symmetrical and mirror each other.

The plate 402 may have one or more recesses 411 on its proximal end 412 for each flap 418 of the screw lock 408 to rotate through a corresponding one of the recesses 411. The recesses 411 may be contiguous to the screw holes 410a to 410d, respectively, to allow the flaps 418 to be positioned over respective screws (not shown) when the screw lock 408 rotates in a given rotational direction (e.g., a counter clockwise direction), thereby locking the screws in place. In the embodiment shown in FIG. 4, the number of the flaps 418 may be four to correspond to that of the screw holes 410a to 410d, and each of four protrusions 413 is disposed between a corresponding pair of adjacent flaps 418.

Figure 5A:
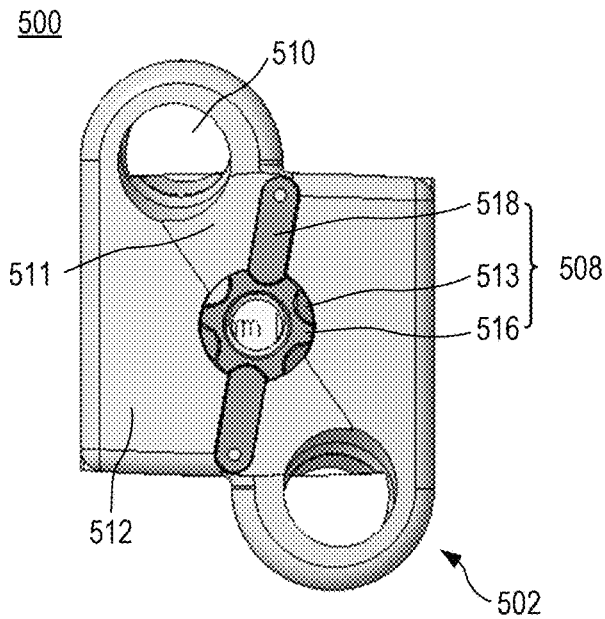
FIGS. 5A and 5B illustrate a front view and a side view of an implant, respectively, according to an embodiment of the present disclosure.
Figure 5B:
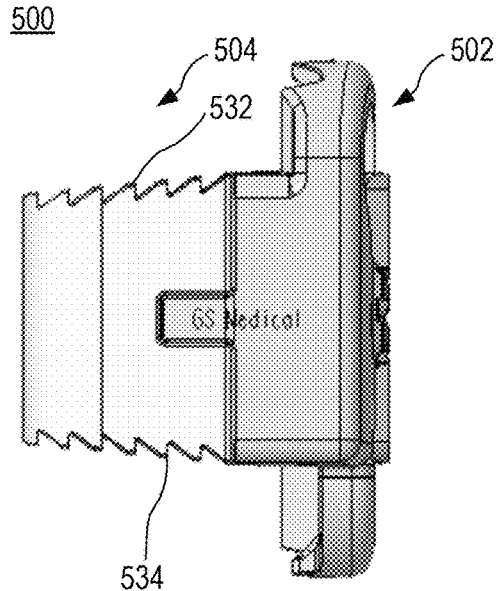

FIGS. 5A and 5B illustrate a front view and a side view of an implant 500, respectively, according to an embodiment of the present disclosure. The implant 500 may have substantially the same features as those of the implant 200 of FIG. 2, except that the implant 500 has a spacer 504 with a height greater than that of the spacer 204 of FIG. 2 and has a plate 502 is different from the plate 202 of FIG. 2. For example, the spacer 504 in FIG. 5B may have a height between upper and lower surfaces 532 and 534 greater than that between upper and lower surfaces 232 and 234 of the spacer 204 of FIG. 2. The plate 502 may have two offset screw holes 510 spaced apart from each other by a distance greater than that of the offset screw holes 210 of FIG. 2. For example, a distance between two centers of the offset screw holes 510 may be greater than that between two centers of the offset screw holes 210 of FIG. 2. In addition, the plate 502 may have a fastener lock 508 with two flaps 518 longer than the flaps 218 of FIG. 2. For example, each of the flaps 518 in FIG. 5A may have a longitudinal length greater than that of each of the flaps 218 of FIG. 2.

The plate 502 may have one or more recesses 511 on its proximal end 512 to allow each flap 518 of the screw lock 508 to rotate through a corresponding one of the recesses 511. The recesses 511 may be contiguous to the screw holes 510, respectively, and the length of the flaps 518 may be sufficiently long to allow the flaps 518 to be positioned over respective screws (not shown) when the screw lock 508 rotates in a given rotational direction (e.g., a counter clockwise direction), thereby locking the screws in place. In an embodiment, a longitudinal length of each of the flaps 518 may be sufficiently long to cover a given portion of a corresponding one of the screw holes 510 when the flap 518 is in a locking position. For example, a portion of each of the flaps 518 may overlap a corresponding one of the screw holes 510, such that a longitudinal length of the overlapped portion of the flap 518 may be in a range from 10% to 30% of a diameter of each of the screw holes 510 when seen in the front view of FIG. 5A. When the length of the overlapped portion of the flap 518 is smaller than 10% of the diameter of each of the screw holes 510, the flap 518 may not sufficiently cover the corresponding one of the screw holes 510 to ensure sufficient locking of a screw (not shown) inserted into the screw hole 510. When the length of the overlapped portion of the flap 518 is greater than 30% of the diameter of each of the screw holes 510, the flap 518 may not have structural properties (e.g., bending modulus to resist a bending moment resulting from a screw loosened in a proximal direction) sufficient to properly keep the screw in place. Although FIGS. 5A and 5B show the flap 518 having a substantially beam structure with the longitudinal length significantly greater than each of a width and a thickness thereof, embodiments of the present disclosure are not limited thereto. For example, each flap (not shown) may have a substantially plate structure with a first length in a radial direction of a ring portion 516 and a second length in a circumferential direction of the ring portion 516, each of the first length and the second length being significantly greater than a thickness of the flap in an axial direction of the ring portion 516.

Figure 6:
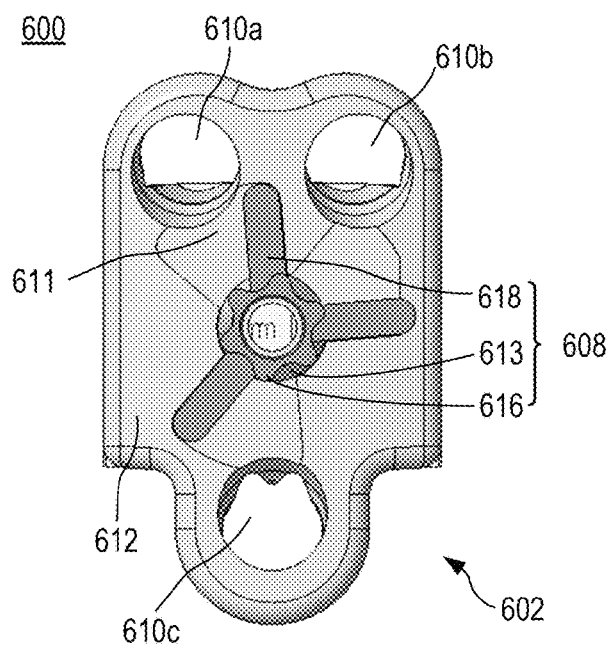
FIG. 6 illustrates a front view of an implant according to an embodiment of the present disclosure.

FIG. 6 illustrates a front view of an implant 600 according to an embodiment of the present disclosure. The implant 600 may have substantially the same features as those of the implant 300 of FIG. 3., except that the implant 600 has a spacer (e.g., the spacer 504 in FIG. 5B) with a height greater than that of the spacer 304 of FIG. 3 and has a plate 602 is different from the plate 302 of FIG. 3. For example, the spacer of the implant 600 may have a height greater than that between upper and lower surfaces 332 and 334 of the spacer 304 of FIG. 3. The plate 602 may have upper offset screw holes 610a and 610b and a lower offset screw hole 610c, and one of the upper screw holes 610a and 610b and the lower screw hole 610c may be spaced apart from each other by a distance greater than that between one of upper offset screw holes 310a and 310b and a lower offset screw hole 310c of FIG. 3. For example, a distance between centers of the upper screw hole 610a and the lower screw hole 610c may be greater than that between centers of the upper screw hole 310a and the lower screw hole 310c of FIG. 3. In addition, the plate 602 may have a fastener lock 680 with three flaps 618 longer than the flaps 318 of FIG. 3. For example, each of the flaps 618 may have a longitudinal length greater than that of each of the flaps 318 of FIG. 3.

The plate 602 may have one or more recesses 611 on its proximal end 612 to allow each flap 618 of the screw lock 608 to rotate through a corresponding one of the recesses 611. The recesses 611 may be contiguous to the screw holes 610a to 610c, respectively, and the length of each of the flaps 618 may be sufficiently long to allow the flaps 618 to be positioned over respective screws (not shown), thereby ensuring secure locking of the screws.

Figure 7:
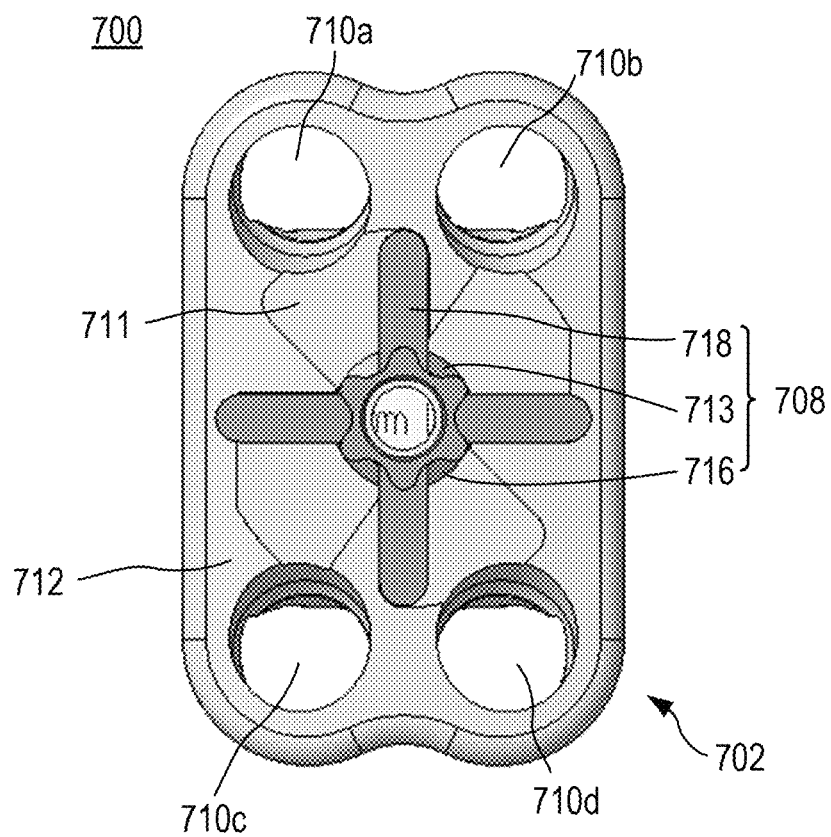
FIG. 7 illustrates a front view of an implant according to an embodiment of the present disclosure.

FIG. 7 illustrates a front view of an implant 700 according to an embodiment of the present disclosure. The implant 700 may have substantially the same features as those of the implant 400 of FIG. 4, except that the implant 700 has a spacer (e.g., the spacer 504 in FIG. 5B) with a height greater than that of the spacer 404 of FIG. 4 and has a plate 702 is different from the plate 402 of FIG. 4. For example, the spacer of the implant 700 may have a height greater than that between upper and lower surfaces 432 and 434 of the spacer 404 of FIG. 4. The plate 702 may have first and second upper offset screw holes 710a and 710b and first and second lower offset screw holes 710c and 710d. The first upper screw hole 710a and the first lower screw hole 710c may be spaced apart from each other by a distance greater than that between a first upper offset screw holes 410a and a first lower offset screw hole 410c of FIG. 4. The second upper screw hole 710b and the second lower screw hole 710d may be spaced apart from each other by a distance greater than that between a second upper offset screw holes 410b and a second lower offset screw hole 410d of FIG. 4. For example, a distance between centers of the first upper screw hole 710a and the first lower screw hole 710c may be greater than that between centers of the first upper screw hole 410a and the first lower screw hole 410c of FIG. 4. In addition, the plate 702 may have a fastener lock 708 with four flaps 718 longer than the flaps 418 of FIG. 4. For example, each of the flaps 718 may have a longitudinal length greater than that of each of the flaps 418 of FIG. 4.

The plate 702 may have one or more recesses 711 on its proximal end 712 to allow each flap 718 of the screw lock 708 to rotate through a corresponding one of the recesses 711. The recesses 711 may be contiguous to the screw holes 710a to 710d, respectively, and the length of each of the flaps 718 may be sufficiently long to allow the flaps 718 to be positioned over respective screws (not shown), thereby ensuring secure locking of the screws.

Figure 8A:
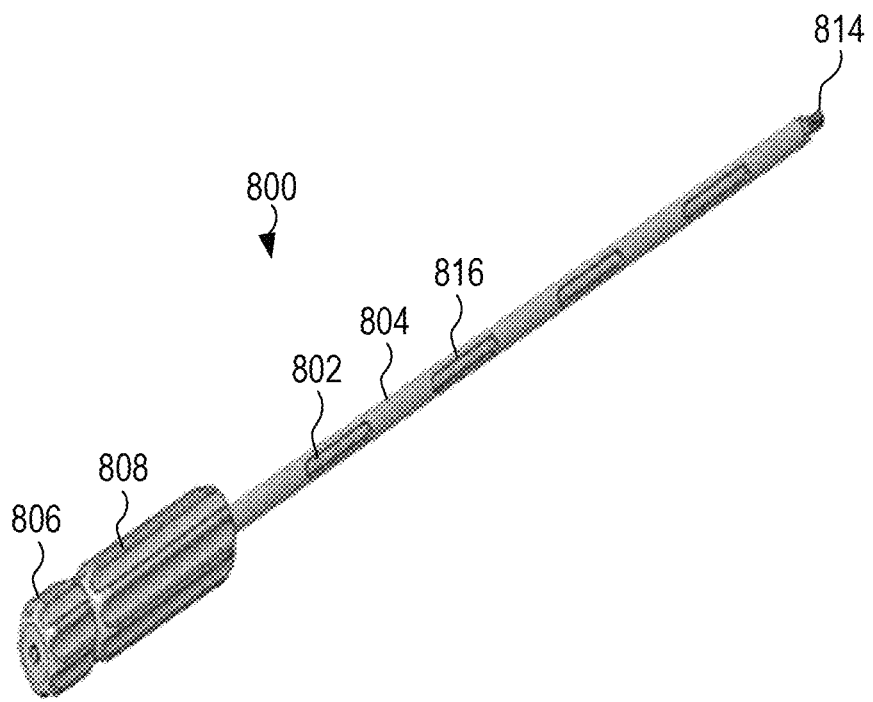
FIGS. 8A and 8B illustrate a perspective view and an exploded view of an inserter, respectively, according to an embodiment of the present disclosure.

FIG. 8A illustrates a perspective view of an inserter 800 according to an embodiment of the present disclosure. The inserter 800 may be a tool used to insert an implant (e.g., the implant 100 in FIGS. 1A to 1C, 200 in FIG. 2, 300 in FIG. 3, 400 in FIG. 4, 500 in FIGS. 5A and 5B, 600 in FIGS. 6, and 700 in FIG. 7) into a treatment region (e.g., a gap between two adjacent vertebrae). The inserter 800 may be removably coupled to the implant. For example, the inserter 800 may be attached to the implant prior to insertion and removed following the insertion. The inserter 800 may have an inner shaft 802, an outer shaft 804, a first handle (e.g., a proximal handle) 806, and a second handle (e.g., a distal handle) 808.

The inner shaft 802 may inserted into a bore (e.g., a bore 810 in FIG. 8B) of the outer shaft 804. The outer shaft 804 may have one or more windows 816 along its longitudinal length. The windows 816 may allow for visibility and cleaning purposes of the inner shaft 802. The inner shaft 802 may be longer than the outer shaft 804. As such, a first end (e.g., a first end 812 in FIG. 8B) and a second end (a second end 814 in FIG. 8B) of the inner shaft 802 may protrude from the outer shaft 804. In an embodiment, the second end 814 may be threadedly coupled to mate with a threaded central hole (e.g., the central hole 114 in FIG. 1A) of the implant. The mating may be facilitated by turning the proximal handle 806. The proximal handle 806 and the inner shaft 802 may be coupled to each other such that the proximal handle 806 turns with the inner shaft 802. The proximal handle 806 and the distal handle 808 may be adjacent to each other when the inner shaft 802 is inserted into the outer shaft 804. The proximal handle 806 and the distal handle 808 may rotate substantially independently of each other. The proximal handle 806 and the distal handle 808 may have cylindrical bodies. Both of the proximal handle 806 and the distal handle 808 may each have a rough surface (e.g., grooves, bumps, protrusions) for facilitating gripping of each of the proximal and distal handles 806 and 808. The proximal handle 806 and the distal handle 808 may be sized differently. In the embodiment shown in FIG. 8A, the distal handle 808 may have a length (e.g., a longitudinal length) greater than that of the proximal handle 806. In other embodiments, the proximal handle 806 may have a length greater than that of the distal handle 808. The proximal handle 806 and the distal handle 808 may have substantially the same diameter or different diameters.

Figure 8B:
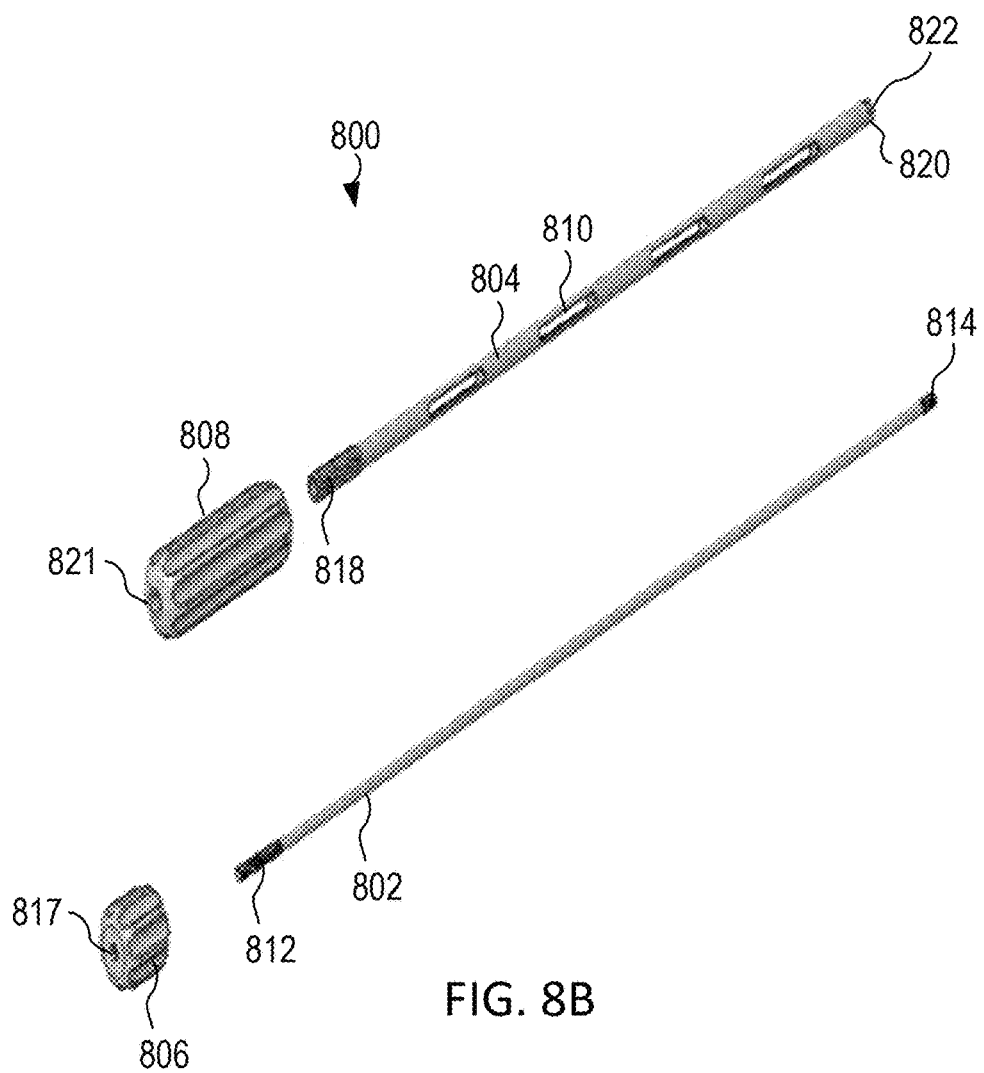

FIG. 8B illustrates an exploded view of the inserter 800 in FIG. 8A according to an embodiment of the present disclosure. As shown in the embodiment of FIG. 8B, the first end 812 of the inner shaft 802 may be threaded to mate with a hole 817 of the proximal handle 806. As shown in the embodiment of FIG. 8B, the hole 817 may entirely extend through the proximal handle 806. In some embodiments, the hole 817 may partially extend through the proximal handle 806. The hole 817 may be threaded to mate with the threaded first end 812 of the inner shaft 802.

The outer shaft 804 may have a first hollow end 818 and a second hollow end 820. As shown in the embodiment of FIG. 8B, the first hollow end 818 may be threaded to mate with a hole 821 of the distal handle 808. The hole 821 may extend through an entirety of the distal handle 808. The hole 821 may be threaded to mate with the first hollow end 818. The second hollow end 820 may have grooves 822 along its circumference. The grooves 822 may be equally spaced apart from each other along the circumference of the second hollow end 820. For example, each of the grooves 822 may extend in a longitudinal direction of the outer shaft 804. The grooves 822 may engage with protrusions (e.g., the protrusions 113 in FIG. 1A) and flaps (e.g., the flaps 118 in FIG. 1A) of a screw lock (e.g., the screw lock 108 in FIG. 1A). For example, the groves 822 may be formed to match recesses formed by the protrusions and flaps of the screw lock. The distal handle 808 and the outer shaft 804 may be engaged such that the distal handle 808 turns with the outer shaft 804. As a result, once engaged with the second end 820 of the outer shaft 804, the flaps may be rotated to be positioned over a screw (e.g., a screw 807 in FIG. 8C) by turning the distal handle 508.

Figure 8C:
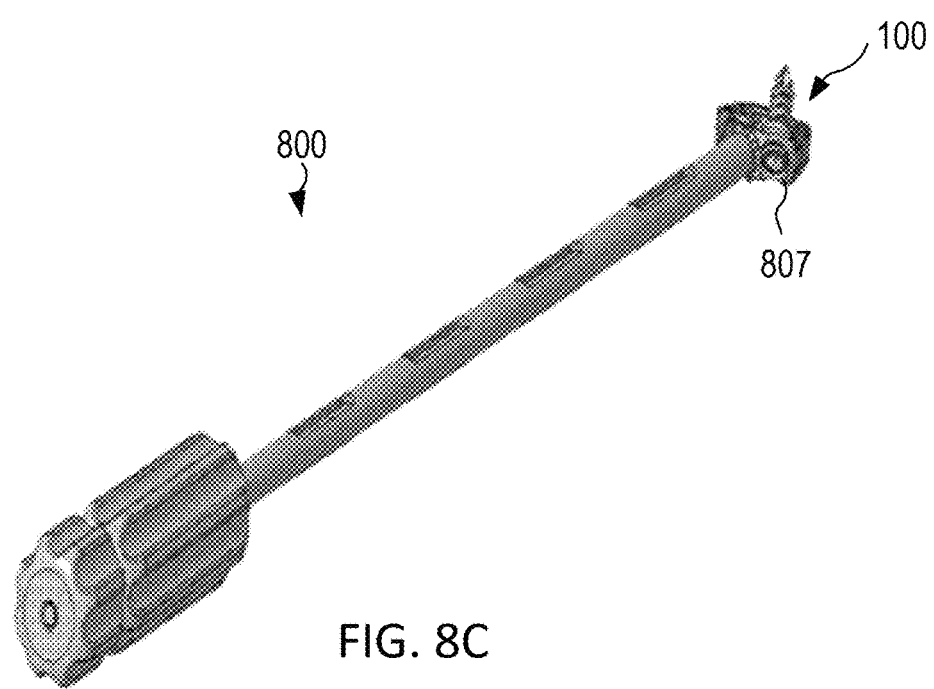
FIG. 8C illustrates the inserter attached to an implant according to an embodiment.

FIG. 8C shows a perspective view of the inserter 800 in FIG. 8A attached to the implant 100 in FIG. 1A according to an embodiment. Referring to FIG. 1A together, the flaps 118 of the implant 100 are positioned over respective screws 807, thereby substantially preventing the screws 807 from coming out in a proximal direction. Hence, after the screw 807 is screwed into a vertebra, the screw 807 may be substantially prevented from slipping out of the vertebra.

The inserter 800 may include the inner shaft 802 to couple the inserter 800 to the central hole 114 of the implant 100 prior to insertion of the implant 100 into a treatment region, by rotating the proximal handle 806 in a first rotational direction (e.g., a clockwise direction). The inserter 800 may further include the outer shaft 804 to place the flaps 118 of the screw lock 108 in a locking position by rotating the distal handle 808 in a second rotational direction (e.g., a counter clockwise direction). After placing the flaps 118 in the locking position, the inserter 800 may be decoupled from the implant 100 by rotating the proximal handle 806 in the second rotational direction. The inserter 800 may include the inner shaft 802 and the outer shaft 804 that perform the insertion process and the locking process together, thereby obviating the need to use two separate devices to perform the insertion and the locking process respectively during surgery.

Figure 9A:
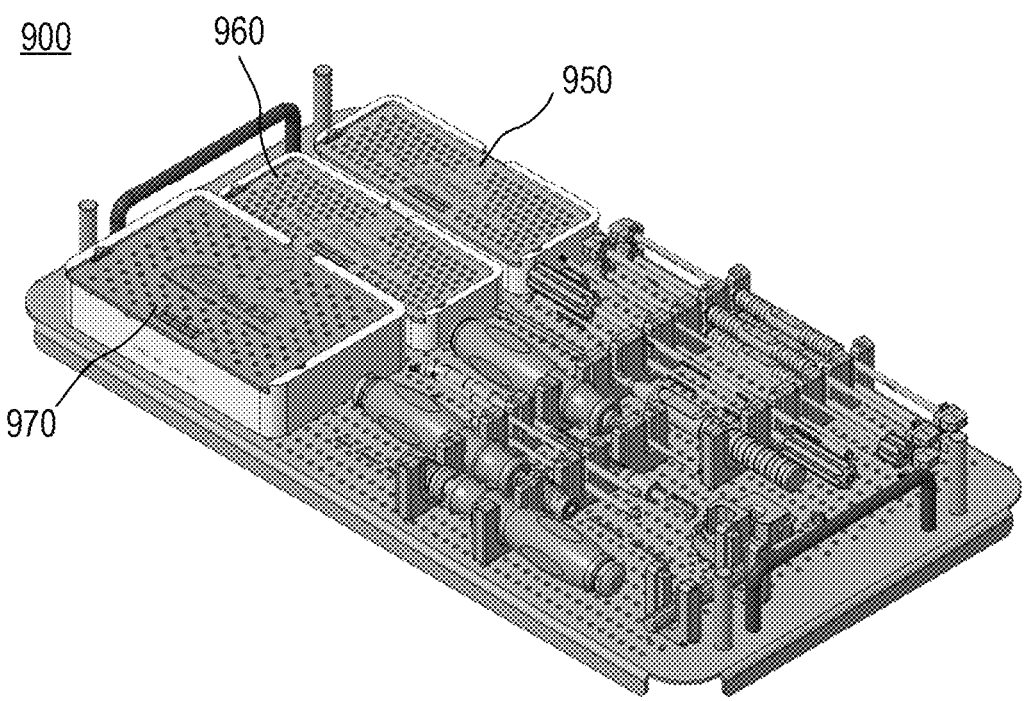
FIGS. 9A and 9B illustrate an upper portion and a lower portion of a tray, respectively, according to an embodiment.
Figure 9B:
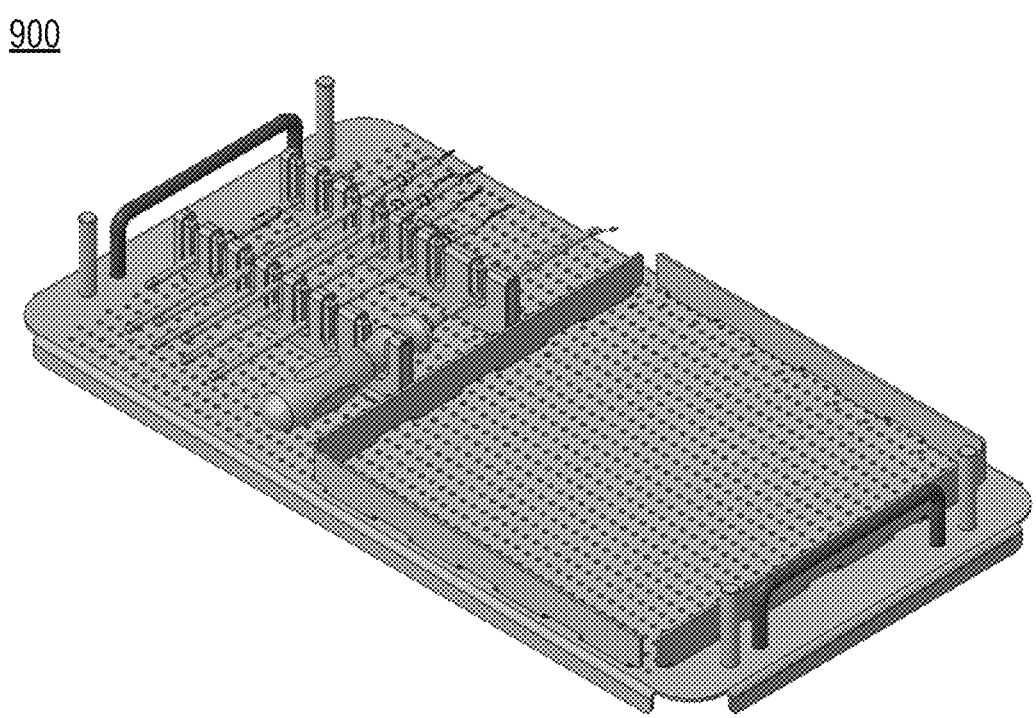

FIGS. 9A and 9B illustrate perspective views of an upper portion and a lower portion of a tray 900, respectively, according to an embodiment. The tray 900 may include a plate caddy 950, a spacer caddy 960, and a screw caddy 970 that accommodate a plurality of plates (e.g., the plate 102 in FIG. 1A), a plurality of spacers (e.g., the spacer 104 in FIG. 1A), and a plurality of screws (e.g., the screw 807 in FIG. 8C), respectively. For example, a user (e.g., a surgeon) may intraoperatively select a plate from the plate caddy 950, a spacer from the spacer caddy 960, and two or screws from the screw caddy 970 and combine the selected plate, spacer, and screws to make a specific implant. In the embodiment of FIG. 9A, the plate caddy 950 is disposed proximate to a top edge of the tray 900, the screw caddy 970 is disposed proximate to a bottom edge of the tray 900, and the spacer caddy 960 is disposed between the plate caddy 950 and the screw caddy 970. However, embodiments of the present disclosure are not limited thereto. In other embodiments, the plate caddy 950, the spacer caddy 960, and the screw caddy 970 may be arranged in an order different from that of the embodiment of FIG. 9A from the top edge to the bottom edge of the tray 900.

The tray 900 may further include other devices for performing cervical discectomy and fusion. In the embodiment of FIGS. 9A and 9B, the tray 900 may include trials, an inserter, Rasp, drivers, a graft impactor, and drills over a top surface of the tray 900, and awls over a bottom surface of the tray 900.

Figure 10:
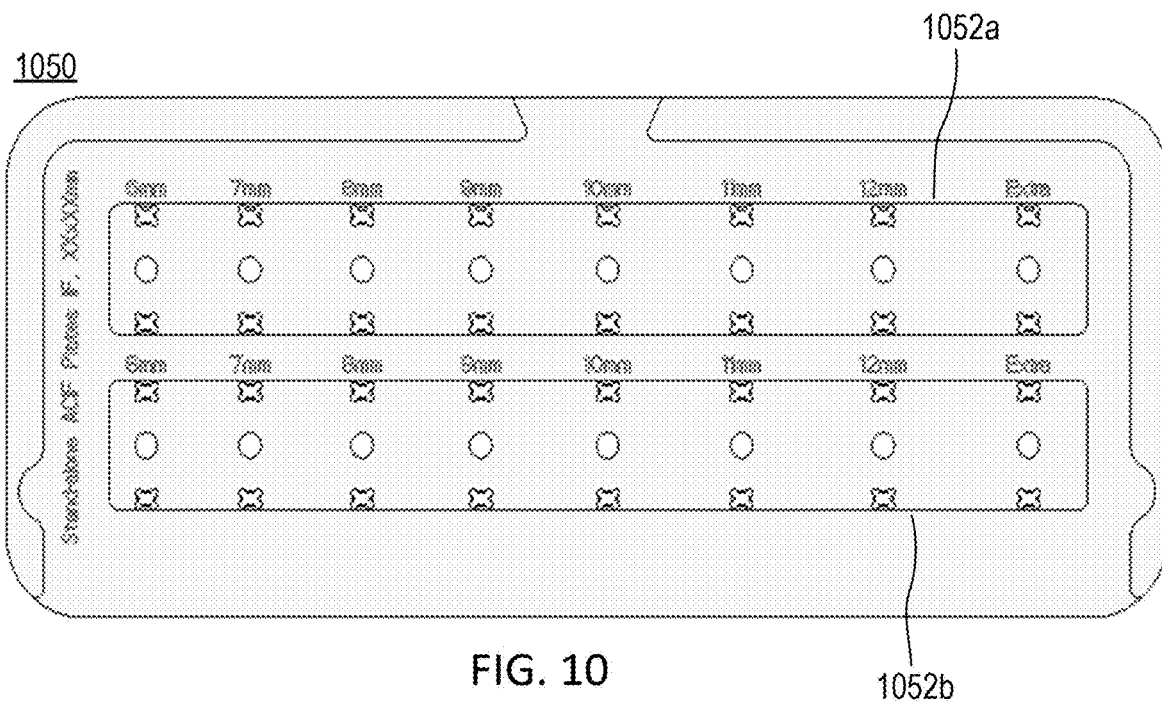
FIG. 10 illustrates a plate caddy according to an embodiment.

FIG. 10 illustrates a plate caddy 1050 suitable for use as the plate caddy 950 in FIG. 9A according to an embodiment. The plate caddy 1050 may include two recessed structures 1052a and 1052b, each of which accommodates a plurality of plates (e.g., the plate 102 in FIG. 1A). In the embodiment of FIG. 10, the plurality of plates may be arranged in an increasing order of size in a specific direction (e.g., a horizontal direction from a left end to a right end with respect to the orientation of FIG. 10) of each of the recessed structures 1052a and 1052b. However, embodiments of the present disclosure are not limited thereto. In another embodiment, the plurality of plates may be arranged in a decreasing order of size in the specific direction. Each of the recessed structures 1052a and 1052b may be further configured to accommodate an extra plate at the right end.

Figure 11:
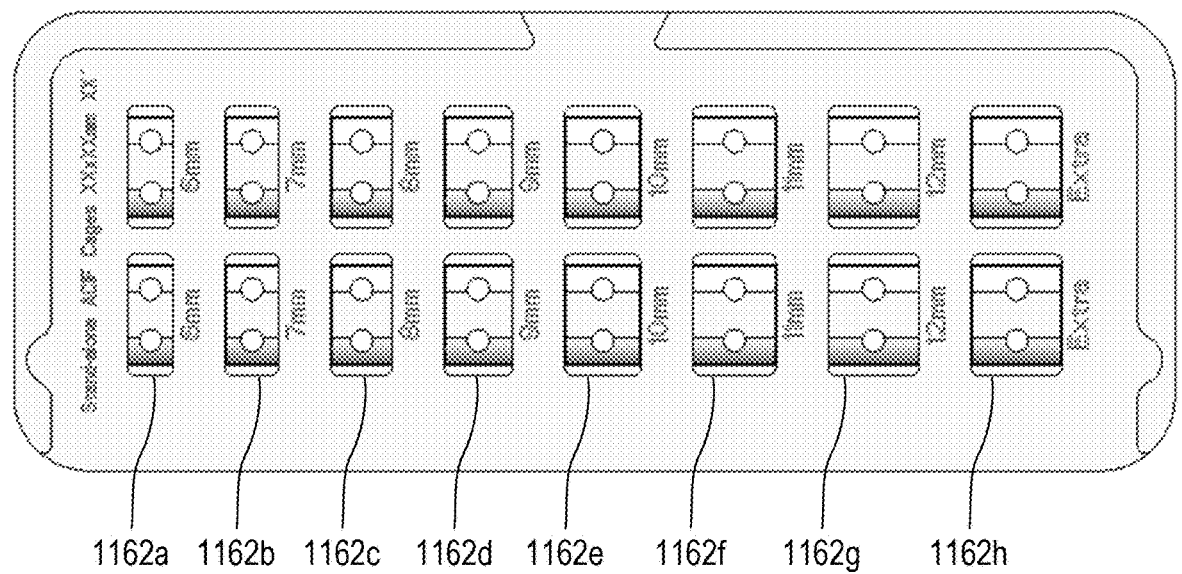
FIG. 11 illustrates a spacer caddy according to an embodiment.

FIG. 11 illustrates a spacer caddy 1160 suitable for use as the spacer caddy 960 in FIG. 9A according to an embodiment. The spacer caddy 1160 may include two row structures, each of which includes a plurality of recesses 1162a to 1162g. The plurality of recesses 1162a to 1162g may be arranged in a specific direction (e.g., a horizontal direction from a left end to a right end with respect to the orientation of FIG. 11) and accommodate a plurality of spacers (e.g., the spacer 104 in FIG. 1A), respectively. In the embodiment of FIG. 11, the plurality of spacers may be arranged in an increasing order of size in the specific direction. However, embodiments of the present disclosure are not limited thereto. In another embodiment, the plurality of spacers may be arranged in a decreasing order of size in the specific direction. Each row structure of the spacer caddy 160 may further include a recess 1162h for accommodating an extra spacer at the right end.

Figure 12:
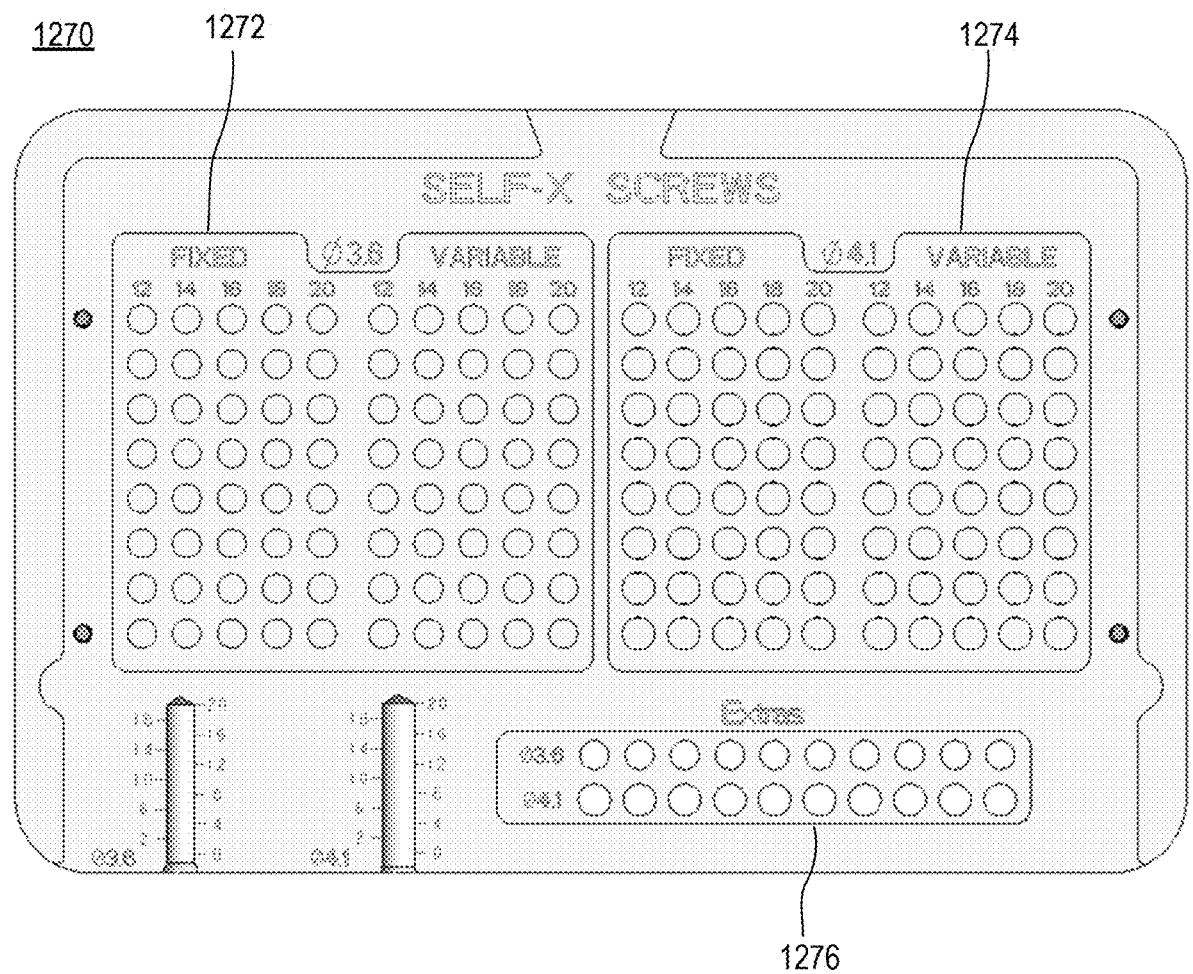
FIG. 12 illustrates a screw caddy according to an embodiment.

FIG. 12 illustrates a screw caddy 1270 suitable for use as the screw caddy 970 in FIG. 9A according to an embodiment. The screw caddy 1270 may include a first region 1272 and a second region 1274, each of which has a plurality of recesses arranged in a matrix form. For example, the plurality of recesses may include a first group of recesses and a second group of recesses, each of the first and second groups of recesses being arranged in a matrix (e.g., 8×5 matrix in FIG. 12), each of the rows (e.g., eight rows in FIG. 12) of the matrix including a plurality of recesses (e.g., five recesses in FIG. 12) to accommodate screws in an increasing order of size in a specific direction (e.g., a left end to a right end of the row in FIG. 12). However, embodiments of the present disclosure are not limited thereto. In another embodiment, each of the rows of the matrix may include a plurality of recesses to accommodate screws in a decreasing order of size in the specific direction. The screw caddy 1270 may further include a third region 1276 having a plurality of recesses to accommodate a plurality of extra screws, respectively. In the embodiment of FIG. 12, the plurality of recesses may be arranged in a 2×10 matrix, each of the two rows of the matrix including recesses to accommodate screws having substantially the same size. However, embodiments of the present disclosure are not limited thereto. For example, each of the rows of the matrix in the third region 1276 may include a plurality of recesses to accommodate screws having different sizes. The screws accommodated in the first, second, and third regions 1272, 1274, 1276 may vary according to embodiments. For example, the screws may include self-drilling screws, self-tapping screws, fixed screws, and variable screws.

Figure 13:
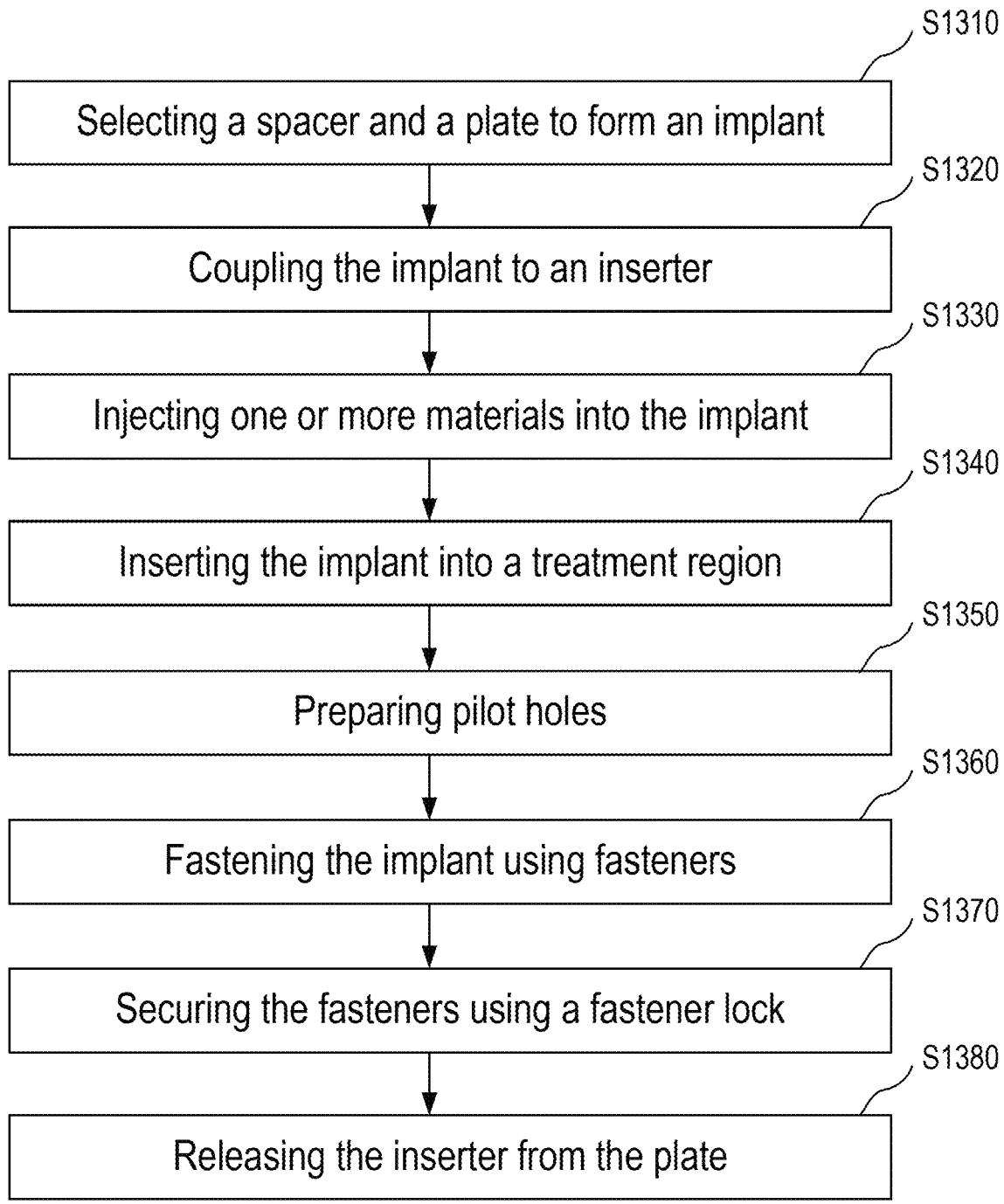
FIG. 13 illustrates a process of using an implant and an inserter during surgery according to an embodiment.

FIG. 13 illustrates a process 1300 of using an implant (e.g., the implant 100 in FIG. 1A) and an inserter (e.g., the inserter 800 in FIG. 8A) during surgery according to an embodiment.

At S1310, a plate (e.g., the spacer 104 in FIG. 1A), a spacer (e.g., the spacer 104 in FIG. 1A), and two or more screws (e.g., the screw 106 in FIG. 8C) may be selected to form a specific implant (e.g., the implant 100 in FIG. 1A). In an embodiment, the plate may be selected from a plurality of plates accommodated in a plate caddy (e.g., the plate caddy 1050 in FIG. 10), the spacer may be selected from a plurality of spacers accommodated in a spacer caddy (e.g., the spacer caddy 1160 in FIG. 11), and the selected plate may be coupled to the selected spacer in the spacer caddy without removing it from the caddy, thereby forming the implant intraoperatively. In an embodiment, a selected spacer may be coupled to a selected plate in a plate caddy to form an implant. Moreover, the two or more screws may be selected from a plurality of screws accommodated in a screw caddy (e.g., the screw caddy 1270 in FIG. 12).

At S1320, the implanter may be coupled to the inserter. In an embodiment, an end of the inserter may engage with a central hole (e.g., the central hole 114 in FIG. 1A) of the plate. For example, the inserter may include an inner shaft (e.g., the inner shaft 802 in FIG. 8B) having a distal end (e.g., the second end 814 in FIG. 8B) threaded to mate with the central hole, and the inner shaft may be rotated in a first rotational direction (e.g., a clockwise direction) to insert the distal end of the inner shaft into the central hole of the plate.

At S1330, one or more materials may be injected into the implant. In an embodiment, these materials may include bone graft material, bone morphogenic protein, or other materials, or a combination thereof, that may be used to facilitate the fusing of the implant to adjacent vertebrae.

At S1340, the implant may be inserted into a treatment region. In an embodiment, the implant may be inserted into a gap between the adjacent vertebrae using the inserter.

At S1350, pilot holes may be prepared using one or more hole preparation devices. In an embodiment, one or more awls (e.g., a straight awl, a sleeved awl, and an angled awl) may be used to penetrate screws holes (e.g., the screw holes 110 in FIG. 1A) and portions of the vertebrae, thereby forming the pilot holes.

At S1360, the implant may be fastened using a plurality of fasteners (e.g., screws). In an embodiment, the screws may be inserted into the screw holes of the plate to fasten the implant to the vertebrae. For example, a first one of the screws may be screwed into a first vertebra (e.g., an upper vertebra) and a second one of the screws may be screwed into a second vertebra (e.g., a lower vertebra), the first and second vertebrae being adjacent to each other.

At S1370, the screws may be secured using a fastener lock (e.g., the screw lock 108 in FIG. 1A). In an embodiment, the fastener lock may include a plurality of flaps (e.g., the flaps 118 in FIG. 1A) each configured to cover a portion of a corresponding one of the screws when the flaps are in a locking position. For example, the inserter may further include an outer shaft (e.g., the outer shaft 504 in FIG. 8B) having an end (e.g., the second hollow end 520 in FIG. 8B) with grooves (e.g., the grooves 522 in FIG. 8B), and the grooves may engage with the plurality of flaps and a plurality of protrusions (e.g., the protrusions 113 in FIG. 1A) to rotate the flaps in a second rotational direction (e.g., a counter clockwise direction), thereby placing the flaps in the locking position.

At S1380, the inserter may be released from the plate. In an embodiment, the inner shaft of the inserter may be rotated in the second rotational direction to release the end of the inner shaft from the central hole of the plate.

While this invention has been described in connection with what is presently considered to be practical embodiments, embodiments are not limited to the disclosed embodiments, but, on the contrary, may include various modifications and equivalent arrangements included within the spirit and scope of the appended claims. The order of operations described in a process is illustrative and some operations may be re-ordered. Further, two or more embodiments may be combined.

What is claimed is:

1. An implant, comprising:
   a plate having a plurality of fastener holes, the plurality of fastener holes being configured to receive a plurality of fasteners, respectively;
   a spacer coupled to the plate and configured to be inserted into a treatment region; and
   a fastener lock movably coupled to the plate and configured to lock the plurality of fasteners,
   wherein the fastener lock includes a plurality of protrusions and a plurality of flaps, the plurality of protrusions and the plurality of flaps together defining recesses that match an end portion of an inserter, the plurality of flaps being configured to overlap the plurality of fasteners, respectively, when the fastener lock rotates in a given rotational direction.

2. The implant of claim 1, wherein the fastener lock further includes a ring portion rotatably coupled to a hole of the plate disposed substantially at a central location of the plate.

3. The implant of claim 2, wherein each of the plurality of flaps extends in a radial direction of the hole of the plate and includes a portion configured to overlap a corresponding one of the plurality of fasteners, the overlapping portion having a length in a range from 10% to 30% of a diameter of each of the plurality of fastener holes.

4. The implant of claim 2, wherein the fastener lock has a first thickness in an axial direction of the ring portion and the plate has a second thickness in an axial direction of the hole, a ratio of the first thickness of the fastener lock over the second thickness of the plate being in a range from 0.15 to 0.35.

5. The implant of claim 2, wherein the recesses defined by the plurality of protrusions and the plurality of flaps are formed on the ring portion to be coplanar with each other.

6. The implant of claim 5, wherein the plurality of protrusions and the plurality of flaps are disposed along a circumference of the ring portion at regular intervals.

7. The implant of claim 2, wherein the plurality of protrusions and the plurality of flaps together define the recesses that match an end of an outer shaft of the inserter, and
   wherein the hole of the plate is configured to be threadedly coupled to an end of an inner shaft of the inserter.

8. The implant of claim 1, wherein the plurality of fasteners includes a first screw and a second screw, and the treatment region is a gap between a first vertebra and a second vertebra, the first vertebra being adjacent to the second vertebra, and
   wherein the plurality of fastener holes is configured to direct the first screw and the second screw into the first vertebra and the second vertebra, respectively.

9. The implant of claim 1, wherein the plate further has a pair of first coupling parts, and
   wherein the spacer has a pair of second coupling parts, the pair of second coupling parts being removably coupled to the pair of first coupling parts of the plate.

10. A system, comprising:
    an implant; and
    an inserter configured to be removably coupled to the implant and insert the implant into a treatment region,
    wherein the implant includes:
      a plate having a plurality of fastener holes, the plurality of fastener holes being configured to receive a plurality of fasteners, respectively;
      a spacer coupled to the plate; and
      a fastener lock movably coupled to the plate and configured to lock the plurality of fasteners,
    wherein the fastener lock includes:
      a ring portion rotatably coupled to a hole of the plate disposed substantially at a central location of the plate; and
      a plurality of protrusions and a plurality of flaps, the plurality of flaps being configured to overlap the plurality of fasteners, respectively, when the fastener lock rotates in a given rotational direction, and wherein the inserter includes:
an inner shaft having a first end and a second end, the second end of the inner shaft being configured to be coupled to the hole of the plate; and
an outer shaft having a first end, a second end, and a bore, the second end of the outer shaft being configured to match recesses defined by the plurality of protrusions and the plurality of flaps of the fastener lock, the inner shaft being inserted into the bore of the outer shaft.

11. The system of claim 10, wherein the second end of the inner shaft is configured to be threadedly coupled to match with the hole of the plate, and
wherein the inserter further includes:
a first handle coupled to the first end of the inner shaft, the first handle being configured to rotate with the inner shaft.

12. The system of claim 11, wherein the inserter further includes:
a second handle coupled to the first end of the outer shaft, the second handle being configured to rotate with the outer shaft.

13. The system of claim 10, further comprising:
a tray including a plate caddy and a spacer caddy, the plate caddy configured to accommodate a plurality of plates, the spacer caddy configured to accommodate a plurality of spacers.

14. A method, comprising:
coupling an inserter to a plate of an implant by rotating the inserter;
inserting the implant into a treatment region;
fastening the implant using a plurality of fasteners; and
securing the plurality of fasteners with a fastener lock of the implant by rotating the inserter,
wherein the inserter includes a first shaft and a second shaft, the first shaft being inserted into a bore of the second shaft, and
wherein the implant is threadedly coupled to a distal end of the first shaft of the inserter by rotating the first shaft in a first rotational direction, and the plurality of fasteners are secured with the fastener lock by rotating the second shaft of the inserter in a second rotational direction, the second rotational direction being opposite to the first rotational direction.

15. The method of claim 14, wherein the fastener lock includes a ring portion rotatably coupled to a hole of the plate disposed substantially at a central location of the plate.

16. The method of claim 15, wherein the fastener lock further includes a plurality of protrusions and a plurality of flaps, and
wherein rotating the second shaft of the inserter in the given rotational direction causes the plurality of flaps to overlap the plurality of fasteners, respectively.

17. The method of claim 16, further comprising engaging a distal end of the second shaft with the plurality of protrusions and the plurality of flaps of the fastener lock to match recesses defined by the plurality of protrusions and the plurality of flaps.

18. The method of claim 14, wherein the plate is selected from a plurality of plates accommodated in a plate caddy, the method further comprising:
selecting a spacer from a plurality of spacers accommodated in a spacer caddy; and
coupling the selected plate and the selected spacer in the spacer caddy to form the implant.

* * * * *